United States Patent [19]

Pickett et al.

[11] 3,940,219

[45] Feb. 24, 1976

[54] COMPACT TELESCOPING TISSUE PROCESSING, EMBEDDING MICROTOME HOLDER AND STORAGE RECEPTACLE

[76] Inventors: John E. P. Pickett, 3323 Pinafore Drive, Durham, N.C. 28212; Thomas D. Kinney, 3120 Devon Road, Durham, N.C. 27707; Gene M. Winders, 5332 N. Willowhaven Drive, Durham, N.C. 27705

[22] Filed: July 11, 1974

[21] Appl. No.: 487,463

[52] U.S. Cl. ............... 425/117; 128/2 B; 220/4 C; 249/160; 425/185
[51] Int. Cl.² ................. B65D 11/00; B65D 81/18
[58] Field of Search ............ 425/117, 185, 84, 470; 249/160; 128/2 B; 220/4 A, 4 B, 4 C, 3.7, 8, 206.5

[56] References Cited
UNITED STATES PATENTS

| | | | |
|---|---|---|---|
| 2,996,762 | 8/1962 | McCormick | 425/117 |
| 3,411,185 | 11/1968 | Pickett | 425/117 |
| 3,412,888 | 11/1968 | Andrews et al. | 220/4 B |
| 3,456,300 | 7/1969 | Pickett | 425/117 |
| 3,816,048 | 6/1974 | Berry et al. | 249/160 |
| R28,165 | 9/1974 | McCormick | 425/117 |

*Primary Examiner*—Ronald J. Shore
*Assistant Examiner*—Carl Rowold
*Attorney, Agent, or Firm*—B. B. Olive

[57] ABSTRACT

A three-part histologic tissue receptacle and embedding structure comprises an identification, open-ended, mold section, a pan section, and a perforated top section which can be slid over the mold and pan sections and retain all three sections in a closed relation. The mold, pan and top sections of the structure may be arranged for service, with the pan telescoped in the mold section, as a perforate, integral, shallow depth, receptacle for holding and transporting the tissue specimens through various liquids during processing, as a mold for embedding the specimen, as a holder for holding the embedded specimen in a microtome during slicing and after slicing, as a housing for holding and protecting the remaining unsliced embedded specimen during extended storage.

8 Claims, 13 Drawing Figures

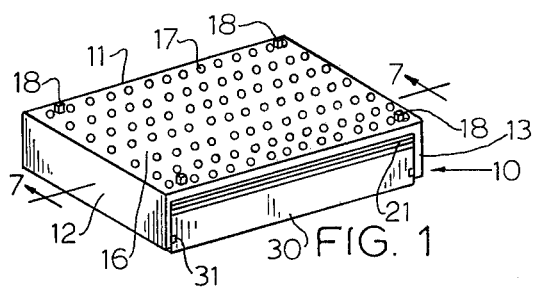
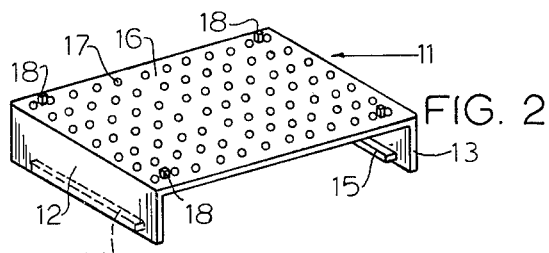
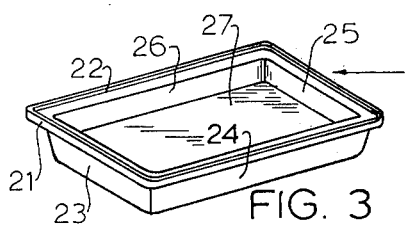
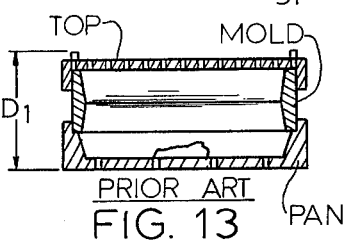
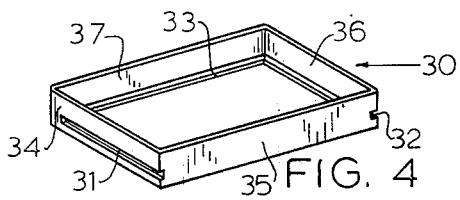
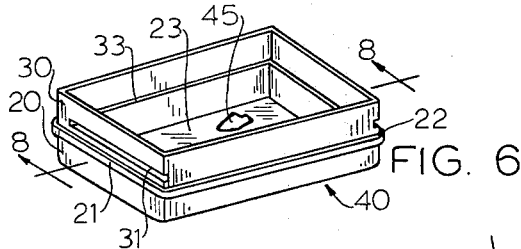
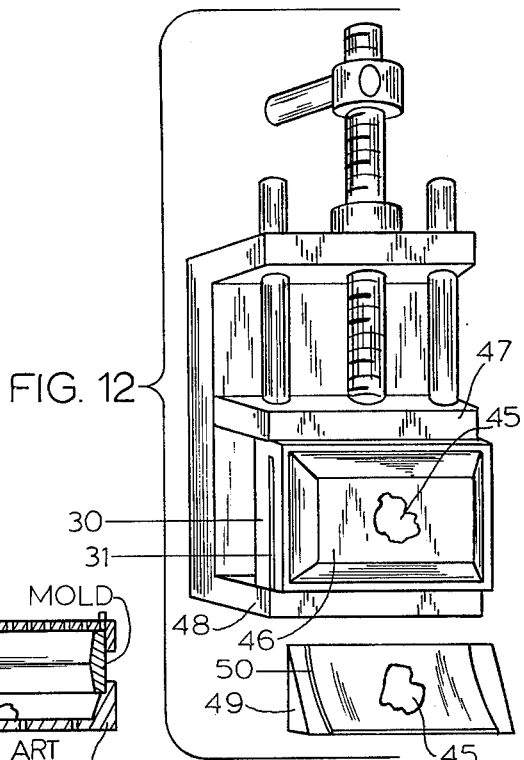
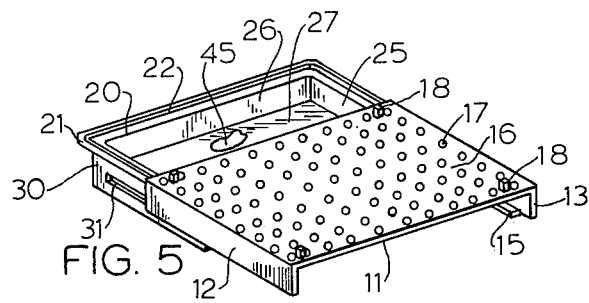
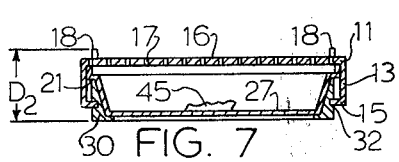
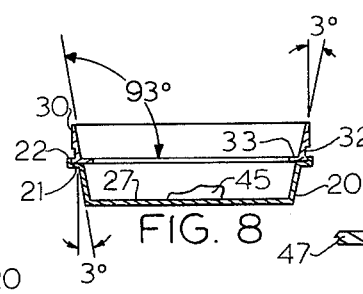
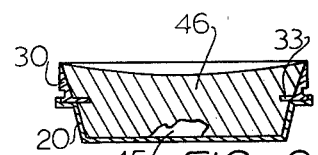
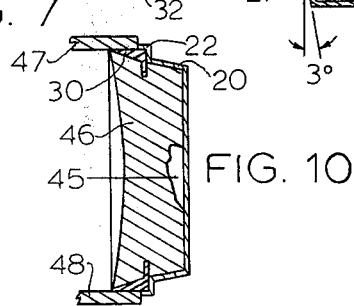
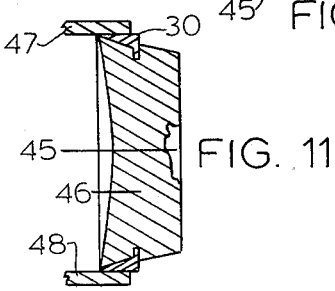

COMPACT TELESCOPING TISSUE PROCESSING, EMBEDDING MICROTOME HOLDER AND STORAGE RECEPTACLE

BACKGROUND OF THE INVENTION

1. Field of the Invention

The invention relates to an improved composite histologic tissue receptacle and embedding structure which serves as an integral, perforate, shallow depth, receptacle for holding tissue during the processing thereof, as a mold for embedding processed tissue in a paraffin body preparatory to mounting in the microtome, as a means for aligning and holding the embedded specimen in the microtome and as a receptacle for protecting and storing the embedded tissue after portions of the same have been severed by the microtome.

2. Description of the Prior Art

A composite tissue receptacle and embedding structure of the type most closely related to this invention is taught by U.S. Pat. No. 3,456,300. The structure taught by this patent includes an open mold, a base pan which is detachably secured onto either open end of the open mold and a perforated top which is detachably secured onto the other end of the open mold all of which forms an integral closure for the specimen. The open mold element of the patent is rectangular in cross section and includes four smooth surfaced perpendicular and interconnecting walls. An outer surface of the upper mold is etched in order to receive indicia by means of an ordinary pencil. The base pan of the patent is shaped substantially like a rectangular open topped box with a thin, heat conducting, flat bottom surface and an indented ledge which extends downwardly from the inside edge of the base pan walls so as to "snap fit" onto either end of the open mold. The flat bottom surface is provided with openings which allow the processing fluids to pass through the composite tissue embedding structure. The perforated top of the patent is detachably secured to the other end of the open mold and consists of a perforated rectangular shaped surface having outwardly projecting sides which "snap fit" over the end of the open mold. The top element in conjunction with the mold and pan elements of the patent forms an integral perforate structure which can be inverted, tilted and otherwise handled without coming apart.

Since the device of the present invention specifically improves on the device of the U.S. Pat. No. 3,456,300, the operation of the device of the patent will next be explained to more fully appreciate the prior art. In operation, a tissue specimen to be pathologically examined is placed in the base pan of the prior patent device without regard to any particular position. One end of the open mold is "snap fastened" to the base pan and the other end of the mold is "snap fastened" to the perforated top to provide the mentioned integral, perforate enclosure for the specimen. The serial number of the tissue specimen is marked by means of a graphite pencil onto an etched surface of the open mold. The mold with the top cover and base pan "snap fastened" to it at either end at this stage provides a perforate tissue processing receptacle. The composite tissue embedding structure is placed sequentially into various treating liquids and finally into a paraffin bath where paraffin is transferred by osmosis into the tissue cells.

As the description proceeds, many similarities will be observed between the construction and use of the device of the U.S. Pat. No. 3,456,300 and the present invention. However, what is important to observe is that the patent device makes no provision for telescoping the pan section into the mold section for reducing the amount of space occupied during processing when the three elements form a processing receptacle. With an increasing use of the patent device the need to process greater and greater numbers of receptacles in the processing chambers has become increasingly critical and important. The relative depth of the three elements when assembled as a processing receptacle thus becomes of increasing importance since this depth to a major extent determines how many receptacles can be processed simultantously. The bottom outside surface is next wiped to remove excess paraffin. At this stage, a thin film of paraffin coats the bottom inside surface of the boat receptacle and while the paraffin is hot and tacky, the perforated top is removed and may be discarded as a disposable item. After adding additional liquid paraffin, the specimen is repositioned on the flat bottom surface of the base pan into a precise cutting position. The paraffin is allowed to harden so that the precise plane of the specimen along which it is to be severed is presented to the microtome blade. The positioning of the specimen is most important for frequently the only means for determining the malignancy of tissue is by properly selecting the plane of severance. As an alternative, the thin coating of paraffin clinging to the bottom surface of the boat receptacle may be allowed to harden and later reheated and the tissue specimen repositioned. In either case, the tissue specimen is positioned while the mold and base pan are "snap fastened" together.

After the tissue specimen is selectively positioned in the base pan, melted paraffin is poured into the base pan through the open end of the open mold to a level substantially adjacent that open end thus completely embedding the tissue specimen. After the paraffin hardens and approaches room temperature, the tissue specimen is presented to the blade of the microtome. Thus, while the base pan remains "snap fastened" to the mold, the composite structure is placed in the jaws of the microtome with the jaws abuted against the exposed surface of the edges of the base pan which act to align the cutting surface of the paraffin block with the microtome blade. After such alignment, the jaws of the microtome are tightened onto the open mold and the base pan is removed which exposes the bottom surface of the block for cutting. After one or several sections are sliced from the tissue specimen by the microtome knife, the base pan is "snap fastened" back onto the open mold so as to cover the exposed tissue specimen surface and prevent the same from becoming soiled or damaged during the usual extended storage for possible later reference to the same patient. At any later time, the tissue specimen may be removed from storage and made available for further sectioning and in the interim the base pan acts as a protective cover.

Further prior art includes devices for processing tissue in plastic or metal perforated containers and for embedding the tissue with paraffin in separate plastic, paper, or metal pans. The device of U.S. Pat. No. 3,674,396, for example, uses a perforated plastic container with a removable metal perforated cover for processing. This metal cover is removed after processing and the tissue specimen is transferred to a metal pan for embedding. The container is then placed in the metal pan and the unit is filled with paraffin for embedding. These devices offer some advantage in providing a relatively shallow depth receptacle for processing but lack the advantage of being able to use the same device for all the steps of processing, embedding, slicing and storing. The devices referred to in U.S. Pat. No. 3,456,300 and in a prior U.S. Pat. No. 2,996,762 mark an advancement over this latter type art since it is desirable to provide an identification mold section which can be used through tissue processing with a perforated top and a pan section, as one unit, for holding and transporting the tissue specimen through the various processing liquids, then as a mold for paraffin embedding the specimen and as a holder for holding the embedded specimen in a microtome during slicing and as a cover for protecting the remaining paraffin tissue block during storage.

Thus, while it can be said that the prior art device described in U.S. Pat. No. 3,456,300 represented a substantial improvement over other prior art devices, there has remained a substantial need to retain the multi-purpose advantages of the patent device but to reduce the amount of space required to process embedded specimens. Stated differently, larger and larger quantities of tissue specimens are being embedded in hospitals, pathology laboratories, and the like, which means that while the device of U.S. Pat. No. 3,456,300 has vastly improved the processing, embedding, and slicing procedures there still remains an critical problem of processing embedded specimens in a minimum of space.

SUMMARY OF THE INVENTION

The compact telescoping tissue processing and embedding receptacle of the invention is comprised of a mold opening at both its top and bottom ends, hereafter known as the identification mold; a pan section which may either be detachably secured to the bottom of the identification mold for molding purposes or fitted downward through the top of the identification mold thereby telescoping within the identification mold during processing for reducing the receptacle depth and a perforated over or top section which encloses both the identification mold and pan telescoped within by means of two appended sidewalls which extend perpendicularly downward from the ends of the perforated top and overlap the outer end walls of the identification mold to a point where these overlapping sidewalls turn perpendicularly inward to form sliding tongue members which operate in grooves that are cut along the outer end walls of the identification mold. The tongue and grooves extend for only a portion of the length of the respective walls in which they are formed which gives the top section a positive stop in one direction and adds to its positive securement. The top sidewalls and mold walls could be otherwise formed so long as the top member can be detachably secured to the mold member.

After the pan section has been telescoped into the mold section and the top section slid into place, the three sections act together to form a perforated enclosure, hereafter called the processing unit, for the tissue specimen. Each element or section may be molded of the same kind of material so long as such material is moldable and inert to the various processing fluids. The exterior surfaces of the sidewalls of the mold section are smooth and provide surfaces to receive indicia by means of an ordinary pencil.

The interior wall surfaces of the identification mold are preferably sloped inwardly at an approximate angle of 03° off vertical which sufficiently increases the thickness of the walls near the bottom to allow the exterior sides of the end walls to be grooved as previously mentioned. The interior and exterior wall surfaces of the identification mold are preferably smooth and uninterrupted by projections, flanges, or the like. However, a narrow and continuous ledge extends inward from the bottom edges of each interior wall of the mold section at an angle of approximately 93° and acts both as a resting shelf for the telescoped pan during processing and as a trapping or gripping member for the hardened paraffin during microtome cutting. The wall surfaces of the mold are otherwise free of flanges, projections, or the like, which minimizes opportunity for tissue damage and enhances opportunity to observe and position the tissue. While the described ledge offers minimum interference and has been found useful to secure the molded block, it is contemplated that the mold interior wall surfaces could be otherwise formed to secure the block. For example, two converging, angled interior walls could be used as in FIG. 7 of U.S. Pat. No. 3,456,300.

The outside width and length of the open mold are preferably limited to about one and five-eighths inches long by one and one-sixteenth inches wide and with a depth of about one-fourth of an inch. The pan section is shaped substantially like an open topped rectangular box composed of four interconnecting walls, a thin heat conducting flat bottom surface, and has a continuous ledge which extends outward from the top edge of each exterior wall. Both exterior and interior walls of the pan section are smooth, uninterrupted and sloped at an angle from top to bottom which corresponds to the slope of the mold walls and allows the pan to telescope within the identification mold as a primary step in the assembly of the processing unit.

The pan ledge which extends outward from the top edges of the exterior walls serves three purposes. During processing, when the pan is telescoped within the identification mold, the ledge provides a positive stop and deters the pan from falling through the mold since it overlaps the top edges of the mold. During embedding, when the pan is positioned underneath the identification mold, the pan ledge acts as a base on which the bottom edges of the walls of the identification mold may rest and be snap-fitted to the pan section. At the same time, the identification mold is prevented from shifting its position on the pan ledge by means of a small, continuous lip which provides the snap-fit and extends perpendicularly upward from the outside edges of the pan ledge to surround a small area of the lower exterior walls of the identification mold. The securing lip also serves to eliminate the need for aligning flanges on the identification mold during microtome cutting since the pan lip furnishes a means of obtaining alignment of the paraffin block with the microtome jaws. The third purpose served by the pan ledge is that of acting as an aid for handling the pan throughout the various steps of processing and embedding. After embedding and following the slicing of the tissue block by the microtome, the pan has the additional function of serving as a protective cover for the exposed block since the pan may, at any time, be resecured to the identification mold.

In order to assemble the processing unit, the pan section is first telescoped into the identification mold.

Following that, the sliding tongue members of the top section are inserted into the open ends of the identification mold grooves and the top section is then pushed forward, its enclosing sidewalls moving along the outside end edges of the pan ledge while the sliding tongue members move along inside the grooves of the identification mold. When the sliding members have been pushed as far as possible into the grooves, the perforated top completely covers the open pan so that the side edges of the top are flush with the side edges of the pan ledge and an integral, perforate processing unit is thereby created. The width and length of the processing unit are preferably limited to about one and one-eighth inches wide and one and thirteen-sixteenths inches long with the depth of the same being about thirteen thirty-seconds of an inch. The depth of the device of the invention when used as a processing unit thus constitutes a major improvement over that taught by U.S. Pat. No. 3,456,300, the depth of which is twice that of the invention. Accordingly, substantially more specimens may be processed in a given space than with the device of the patent.

In use, the specimen accession number is written on one etched surface of the exterior walls of the identification mold. The tissue which is to be pathologically examined is placed in the pan section without regard to any particular position and the perforated top section is slid into place as previously explained. The processing unit thus created is capable of serving all purposes conventionally served by the processing receptacle taught by U.S. Pat. No. 3,456,300, yet the depth or thickness of the invention remains one-half that of the prior art. A plurality of processing units are then stacked side-by-side in a tissue processing basket which in turn is placed in an automatic tissue processor where the specimens undergo exposure to various liquids such as alcohol and xylene which prevent autolization and prepare the specimen for embedding. As a final step within the processor, the specimens are bathed in liquid paraffin whereupon quantities of paraffin are transferred by osmosis into the tissue cells as previously explained. The basket is then removed from the processor and the receptacle units are removed and placed on a heated surface. The top section is removed from each unit by sliding the tongue members backwards out of the grooves. The heretofor processing unit now becomes the embedding unit as the relative positions of the pan and the identification mold are reversed. This is accomplished by removing the pan from its telescoped positioned within the mold and then placing the mold on top of the pan where it rests on the pan ledge and is snugly held in place by the surrounding lip which extends upward from the ledge. This embedding unit is then partially filled with melted paraffin and placed on a cold surface. As the paraffin begins to solidify, the tissue specimen is respositioned into a precise cutting position. The paraffin is allowed to harden so that the precise plane of the specimen along which it is to be severed is presented to the microtome blade. The positioning of the specimen is most important, as previously explained, for frequently the only means for determining the malignancy of tissue is by properly selecting the plane of severance. As an alternative, the paraffin which partially fills the pan may be allowed to harden and at a later time may be reheated and the tissue specimen repositioned. In either case, the tissue specimen may be positioned while the identification mold is securely resting upon the pan ledge since the mold itself is free of internal projections which might otherwise interfere with such repositioning.

After the tissue specimen has been selectively positioned in the pan, melted paraffin is poured into the pan through the open end of the identification mold to a level which is substantially adjacent that open end thus completely embedding the tissue specimen after accounting for the shrinkage of the paraffin upon solidification. The paraffin is allowed to cool and the cooling may be hastened by placing the pan and identification mold on a cold surface. After the paraffin has hardened and been cooled with ice, or otherwise, the tissue specimen is adapted to be presented to the blade of the microtome. Thus, while the identification mold remains snap-fit secured to the pan ledge, the composite structure is placed in the jaws of the microtome whereby the jaws abut against the securing lip of the pan ledge which acts to align the cutting surface of the paraffin block with the microtome blade.

After such alignment, the jaws of the microtome are tightened onto the identification mold and the pan is removed. The tissue block at this stage is prevented from being pulled from the mold by the gripping effect of the internal identification mold ledge and the removal of the pan exposes the bottom surface of the block for cutting. After one or several sections have been sliced from the tissue specimen by the microtome knife, the pan may again be secured onto the identification mold in a snap-fit relation so as to cover the exposed tissue surface and present the same from becoming soiled or damaged during the usual extended storage for possible later reference to the same patient. At any later time, the tissue specimen may be removed from storage and made available for further sectioning by removing the same from the storage drawer and inserting it into the microtome as described above. The absence of flanges on the identification mold as found in the prior art plus the compact size of the invention facilitates storage of more units in the same space.

Therefore, the object of the invention is generally to improve on the device of U.S. Pat. No. 3,456,300 while retaining its many advantages but principally to substantially reduce the amount of space required when processing with such a device as a receptacle.

Other objects and advantages of this invention will become apparent when the following detailed description is read in conjunction with the appended drawings and claims. A preferred embodiment of this invention will now be described with reference to the accompanying drawings, in which:

DESCRIPTION OF THE DRAWINGS

FIG. 1 is a perspective view of the compact-telescoping processing and embedding unit of this invention showing the various elements in an interconnected relationship as they are assembled to form the processing unit.

FIG. 2 is a perspective view of the perforated top section.

FIG. 3 is a perspective view of the pan section.

FIG. 4 is a perspective view of the identification mold section.

FIG. 5 is a perspective view of the various elements and the identification mold as they are assembled to form the processing unit.

FIG. 6 is a perspective view of the pan section and the identification mold as they are assembled to form the embedding unit.

FIG. 7 is a section view taken along lines 7—7 of FIG. 1 and showing the invention structure as it appears in service as a receptacle for receiving and processing a tissue specimen through the various processing liquids.

FIG. 8 is a section view taken along lines 8—8 of FIG. 6 and showing the invention structure as it appears in service as the embedding unit prepared to receive the melted paraffin for embedding the tissue specimen in a paraffin block.

FIG. 9 is a section view of the embedding unit with the tissue specimen embedded in the solidified paraffin.

FIG. 10 is a section view showing the identification mold portion of the finished unit clamped between opposed jaws of a microtome with the lip of the pan ledge abutting against the jaws and thereby acting as a means of aligning the embedded specimen to be sliced by the microtome cutting blade.

FIG. 11 is a section view like FIG. 10 with the pan section removed so as to present the tissue specimen to the knife of the microtome.

FIG. 12 is an enlarged pictorial view of the tissue specimen at it appears embedded in the exposed paraffin block and mounted for cutting by the microtome.

FIG. 13 is a section view comparable to FIG. 7 of the prior art device of the U.S. Pat. No. 3,456,300 in use as a receptacle.

DETAILED DESCRIPTION OF THE PREFERRED EMBODIMENT

The first element of the compact-telescoping processing and embedding structure when assembled as the compact processing unit 10 is a perforated top 11 which includes a rectangular central plate 16 and two perpendicularly downward extending sidewalls 12 and 13 which are integrally connected to plate 16 along the end edges thereof. Sliding tongue members 14 and 15 are inward turning, perpendicular continuations of sidewalls 12 and 13 but are of a shorter length than sidewalls 12 and 13. Perforated top 11 serves as a means of admitting the various processing fluids, including hot liquid paraffin, into the compact processing unit 10 and the perforations are provided by a plurality of openings 17 through which the various liquids may pass. Perforated top 11 is preferably molded from a thin resilient plastic such as a polyformaldehyde resin or metal which is inert to and will not float in the various processing liquids and which will withstand the usual processing temperatures. Top 11 may be disposable if made of plastic and reusable if made of metal. Further, top 11 is also provided with a plurality of knobs 18 which extend outwardly from the top surface of plate 16 and which provide means for spacing several of the structures 10 from each other when the same are stacked side by side during the fixation process and which allows the fixation fluids to enter and leave the openings 17.

The second element of the compact structure 10 is the pan section 20, which like top 11, may also be molded of polyformaldehyde resin material or of metal and is comprised of a thin, heat conducting bottom wall 27, the outside surface of which may be etched to receive indicia, and sidewalls 23, 24, 25 and 26 which intersect bottom wall 27 at an approximate off-vertical angle of 03° from top to bottom to form an open topped rectangular box. The 03° inward angle of sidewalls 23, 24, 25 and 26 corresponds to a similar slope of the outer walls of pan section 20 and enables pan section 20 to telescope snugly within sidewalls 34, 35, 36 and 37 of identification mold 30. The upper outer edges of sidewalls 23, 24, 25 and 26 of pan section 20 are provided with a continuous generally horizontal exterior ledge or flange 21, which forms an angle of approximately 93° with the sidewalls 23, 24, 25 and 26. A shallow, continuous lip 22 extends perpendicularly upward from the outside edges of the flange or pan ledge 21 such that when pan section 20 is telescoped within identification mold 30 for processing, pan ledge 21 overlaps and rests on the top edges of the identification mold sidewalls 34, 35, 36 and 37. Later, when the relative positions of pan section 20 and identification mold 30 are reversed in order to form the embedding unit shown in FIG. 6, pan ledge 21 acts as a base on which the bottom edges of identification mold sidewalls 34, 35, 36 and 37 may rest. At the same time, lip 22 both prevents identification mold 30 from shifting position on pan ledge 21 and effects a snug, snap-fit joint between pan section 20 and identification mold 30 which prevents the leaking of paraffin during embedding. Whether pan section 20 is molded of polyformaldehyde resin or metal, pan bottom 27 should have the character of thinness in the order of from 0.020 to 0.050 inch thick to rapidly conduct heat and rapidly cool the specimen as required just prior to embedding.

The third and previously mentioned element of the compact processing structure 10 is an open mold 30, referred to as identification mold 30, which, like top 11 and pan section 20, is preferably also molded of polyformaldehyde resin material and is comprised essentially of four integrally connected sidewalls 34, 35, 36 and 37 whose exterior surfaces intersect at right angles so as to form an open-ended box which is rectangular in cross section, both longitudinally and laterally. The exterior surfaces of sidewalls 35 and 37 are flat and one or both are etched to receive appropriate indicia. The exterior surfaces of sidewalls 34 and 36 are also flat but are interrupted by longitudinal grooves 31 and 32 which extend respectively from the exterior intersection of sidewall 34 and sidewall 35 and from the exterior intersection of sidewall 36 and sidewall 35 and terminate at equidistant points on both sidewalls 34 and 36, said points lying just short of the exterior intersections of sidewalls 34 and 37 and sidewalls 36 and 37. The lower edges of sidewalls 34, 35, 36, and 37 are provided with a short, continuous interior mold ledge 33, which extends inward from the lower edges of said sidewalls 34, 35, 36 and 37. The interior surfaces of sidewalls 34, 35, 36 and 37 are smooth and intersect identification mold ledge 33 at an approximate angle of 93°. This inward angle relation produces a greater thickness for the lower portions of sidewalls 34 and 36 thereby enabling sidewalls 34 and 36 to accommodate grooves 31 and 32. Identification mold ledge 33 serves as a resting shelf for the outer edges of pan bottom 27 when pan section 20 is telescoped within identification mold 30. A further and more important function of identification mold ledge 33 is to act as a gripping or trapping member for securing paraffin block 46 to identification mold 30 as best shown in FIGS. 9, 10 and 11 which eliminates the need for projections or like interior configurations to secure the molded block to the interior wall surfaces of identification mold 30, presents the least opposition to the flow of processing fluids and makes it practical to position the tissue specimen 45 in pan 20 when identification mold 30 is seated atop pan section 20 as shown in FIG. 6. While similar advantages are to be found in the device of U.S. Pat.

No. 3,456,300, they have not been previously obtained in a shallow depth, multi-purpose unit as with the present invention.

In operation, pan section 20 is first telescoped within identification mold 30.

It should be noted that the manner in which the mold and pan members are shaped with the described interior angled wall and block securing ledge, the pan section can be inserted into the mold member only through the open end of the mold member opposite ledge 33 and the pan section is blocked from entry through the opposite end of the mold member. Further, the described tongue and groove securing arrangements for securing the top member operate when the pan section is properly nested, thus proper assembly of the receptacle is always assured.

The specimen accession number is next written on one or both of the etched exterior surfaces of identification mold walls 35 and 37. Note here that the use of the identification mold as part of the processing receptacle during processing insures that the mold and specimen always stay together and that the specimen is always identifiable by indicia on the mold. This is particularly significant since the top is normally discarded after processing and the pan section becomes separated from the specimen during slicing. Tissue specimen 45 is then placed on pan bottom 27 after which tongue members 14 and 15 of top 11 are aligned with and inserted into the open ends of grooves 31 and 32 of identification mold 30. Top section 11 is then slid into place as indicated in FIG. 5. Completion of the sliding action results in the creation of the compact, shallow depth perforate processing unit 10 of FIG. 1. It is contemplated that a plurality of processing units 10 will be stacked in a tissue processing basket with knobs 18 spacing adjacent compact processing units 10.

What should be particularly appreciated at this point in the description is that the improved telescoping pan-mold and top securing arrangement of the present invention provides a processing unit 10 of relatively shallow depth as compared to the processing device of U.S. Pat. No. 3,456,300. To illustrate, FIG. 13 shows the patent device and it will be noted that the receptacle depth $D_1$ is obtained by effectively stacking the covered mold on the pan of the patent device. In comparison, the receptacle depth $D_2$ of the invention is effectively only the depth of the pan. Thus, in the preferred embodiment previously described, the receptacle depth of the invention device for purpose of processing is substantially half that of the patent device. Therefore, in a given space with the invention receptacle, twice as many receptacles and twice as many specimens may be processed. However, as with the patent device, the identifying mold always stays with the specimen, thus the critical identification, once properly applied to the mold cannot be lost or separated from the specimen except by very gross error in procedure.

The processing basket, once filled with the processing units 10, is then placed within an automatic tissue processor where the tissue specimens 45 undergo exposure to various processing liquids which enter and exit through perforations 17 in top 11. The final liquid to which tissue specimen 45 is exposed is hot paraffin whereupon quantities of the melted paraffin are transferred by osmosis into the tissue cells. The basket is then removed from the processor and the units 10 are removed and placed on a heated surface. Top section 11 is removed by a reverse sliding action wherein sliding tongue members 14 and 15 are slid backwards out of grooves 31 and 32 of identification mold 30.

After removal of top 11, the heretofore compact processing unit 10 is now ready to be transformed into the embedding unit 40 of FIG. 6. This is accomplished by removing pan 20 from its telescoped position within identification mold 30 and then placing identification mold 30 on top of pan 20 where it rests on pan ledge 21 and is snap-fit secured in this position by lip 22. The structure of the now assembled embedding unit 40 is shown in FIG. 6. Embedding unit 40 is next partially filled with liquid paraffin and transferred to a cold surface whereupon the paraffin begins to solidify. As the paraffin solidifies, tissue specimen 45 is repositioned so that the precise plane of cutting may be achieved. After tissue specimen 45 has been properly repositioned on bottom 27 of pan 20, embedding unit 40 is placed under an orifice which then supplies additional liquid paraffin to embedding unit 40, such liquid paraffin filling embedding unit 40 to a level substantially level to the open end of identification mold 30. The paraffin is then cooled to form paraffin block 46 which contracts and assumes the shape shown in FIG. 9, completely embedding specimen 45. It can be seen from FIG. 9 that paraffin block 46 extends above identification mold ledge 33 so that upon removal of pan section 20, paraffin block 46 is securely trapped within identification mold 30.

Embedding unit 40, which now includes paraffin block 46, is ready to be positioned between opposing microtome jaws 47 and 48. This is accomplished by inserting sidewalls 35 and 37 of identification mold 30 between microtome jaws 47 and 48, as shown in FIG. 10, until selected edges of pan lip 22 abut against the ends of jaws 47 and 48. It is this abutment of lip 22 which acts to correctly align embedding unit 40 so that when pan section 20 is removed from block 46, as shown in FIG. 11, block 46 will be substantially parallel to microtome blade 49 as shown in FIG. 12. This arrangement, as previously mentioned, eliminates the need for aligning flanges on identification mold 30 but nevertheless results in accurate alignment. When pan 20 has been removed from block 46, as illustrated in FIGS. 11 and 12, tissue slices 50 are cut from block 46 and after the required number of slices 50 have been taken from block 46, pan 20 may be repositioned onto identification mold 30 so as to protect tissue specimen 45 and to provide abutting surfaces if it is ever desirable to replace and realign paraffin block 46 in microtome jaws 47 and 48 for further severance of the same.

We claim:

1. A composite histologic tissue structure useful for transporting a tissue specimen through processing fluids during processing, providing a mold for embedding the specimen, holding the embedded specimen during microtome cutting and covering the remaining embedded specimen following cutting, comprising:
    a. a rectangular open rigid mold and microtome block holding member formed by interconnecting smooth surfaced rectangular end and sidewalls with the interior wall surfaces thereof being formed with means for securement of a molded block thereon and the exterior wall surfaces thereof being formed to provide an indicia marking area to identify the specimen;
    b. a rectangular pan receptacle and storage cover member formed by a thin rectangular bottom wall and interconnecting rectangular end and sidewalls, said pan and mold members being dimensioned such that said pan member walls may rest within said mold member walls during processing through processing fluids, the wall edges on one open end of said mold member having means for being detachably secured to the top wall edges of said pan member during the molding of said block; and c. a top receptacle member formed by a central rectangular perforated wall and interconnecting rectangular sidewalls extending perpendicularly from the edges thereof, said top member sidewalls having means for detachably securing said mold member to said top member with said central wall covering said pan member while said pan member is resting within said mold member whereby said top member may combine with said mold and pan members to form a perforate receptacle having the depth of said pan section for purposes of processing through said liquids;

said mold and pan members in combination with said top member providing a receptacle for transporting the tissue specimen through the processing fluids, said mold member in combination with said pan member providing an embedding unit for molding and housing a paraffin body of depth greater than that of said receptacle used in processing, said mold member providing an exterior surface for clamping said mold member and the specimen embedded therein between the opposing jaws of a microtome clamp for presenting the embedded specimen to a microtome blade for cutting, and said mold member in combination with said pan member providing a housing for protecting the remaining specimen following cutting.

2. The structure of claim 1 wherein said mold member includes a ledge formation on the interior wall surfaces thereof and proximate one open end thereof, said ledge formation serving as said means for securing said block.

3. The structure of claim 1 wherein said detachable securement means for said mold member and top member include interlocking tongue and groove formations on the detachably secured surfaces thereof.

4. The structure of claim 3 wherein said groove formations are formed in said mold member exterior end wall surfaces, said tongue formations are formed on the interior surfaces of said top member sidewalls and said tongue and groove formations each extend from a respective surface edge for a distance less than the length of the corresponding surface on which so formed whereby said top member tongue formations may enter said groove formation from only one direction and be positively stopped after appropriate movement in such direction.

5. The structure of claim 1 wherein said pan member includes an outwardly extending flange surrounding its open end and including a lip formation therein and said mold member walls adapt to resting on said flange and to being snap-fitted to said lip formation.

6. The structure of claim 5 wherein with said pan member detachably secured to said mold member and said mold member containing said molded block, said flange provides a positive stop for correct mounting of said mold member in a microtome preparatory to slicing of said specimen.

7. The structure of claim 6 wherein said mold member includes a ledge formation on the interior wall surfaces thereof and proximate one open end thereof, said ledge formation serving as said means for securing said block and wherein said mold member interior wall surfaces and said pan member wall surfaces are sloped in a manner enabling said mold member interior wall surfaces to form a continuation of said pan member interior wall surfaces when said mold member is detachably secured to said pan member.

8. The structure of claim 1 wherein said mold and pan members are shaped to allow said pan member to be inserted through one open end of said mold member and to be prevented from entry through the opposite open end of said mold member and said top member is securable to said mold member only when so inserted thereby insuring correct assembly of said receptacle.

* * * * *

UNITED STATES PATENT OFFICE
CERTIFICATE OF CORRECTION

Patent No. 3,940,219  Dated February 24, 1976

Inventor(s) John E. P. Pickett, et al.

It is certified that error appears in the above-identified patent and that said Letters Patent are hereby corrected as shown below:

In line 8 of the Abstract "moid" should be --mold--.

In Col. 2, line 14, "simultantously" should be --simultaneously--.
(Our error)

In Col. 2, line 43, "abuted" should be --abutted--. (Our error)

In Col. 3, line 29, "an" should be --a--. (Our error)

In Col. 3, line 43, "over" should be --cover--.

In Col. 6, line 30, "present" should be --prevent--.

Signed and Sealed this

Twenty-seventh Day of July 1976

[SEAL]

Attest:

RUTH C. MASON
Attesting Officer

C. MARSHALL DANN
Commissioner of Patents and Trademarks